United States Patent [19]

Edwards

[11] Patent Number: 5,174,154

[45] Date of Patent: Dec. 29, 1992

[54] ISOMETRIC FORCE MEASURING DEVICE

[75] Inventor: Glenn R. Edwards, Palo Alto, Calif.

[73] Assignee: Greenleaf Medical Systems, Inc., Palo Alto, Calif.

[21] Appl. No.: 581,482

[22] Filed: Sep. 12, 1990

[51] Int. Cl.⁵ .................................. A61B 5/22
[52] U.S. Cl. ..................... 73/379; 128/774
[58] Field of Search ............ 73/379, 862.58, 862.64, 73/862.65, 862.68; 128/26, 774, 740; 341/34; 269/481

[56] References Cited

U.S. PATENT DOCUMENTS

| 3,277,718 | 10/1966 | Ruge | 73/862.65 |
| 3,695,100 | 10/1972 | Mitchell | 73/862.58 |
| 3,866,464 | 2/1975 | Franklin | 73/862.58 |
| 4,159,107 | 6/1979 | McArthur | 269/48.1 |
| 4,467,815 | 8/1984 | O'Brien et al. | 128/740 |
| 4,770,050 | 9/1988 | Hafner et al. | 73/862.68 |

OTHER PUBLICATIONS

Brochure from Therapeutic Instruments.
Illustrates a pinch meter from North Coast Medical, Inc.
Brochure from J. A. Preston Corp.

Primary Examiner—Michael Razavi
Assistant Examiner—Elizabeth L. Shopbell
Attorney, Agent, or Firm—Kirkpatrick & Lockhart

[57] ABSTRACT

An isometric force-measuring device is comprised of first and second opposed force-bearing surfaces. An incompressible, nonfluid material is positioned between the first and second surfaces. The material is capable of building up pressure in response to the application of force to the force-bearing surfaces. A pressure transducer is responsive to the pressure stored in the material for producing an output signal representative of the force.

1 Claim, 3 Drawing Sheets

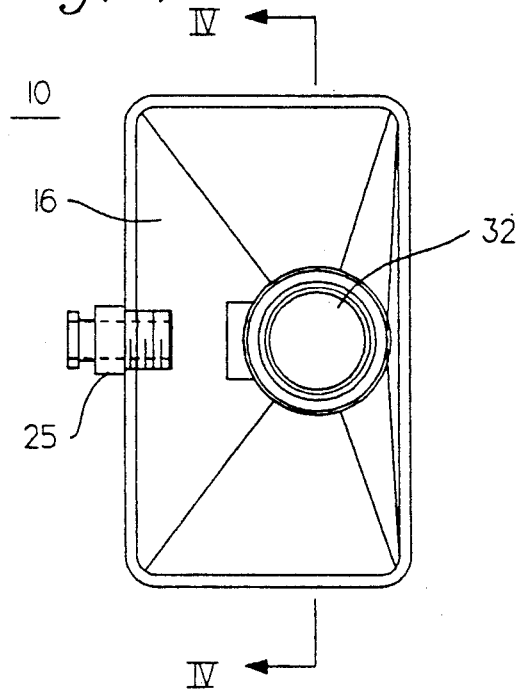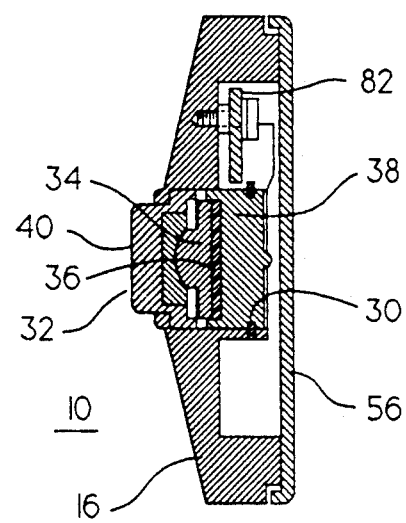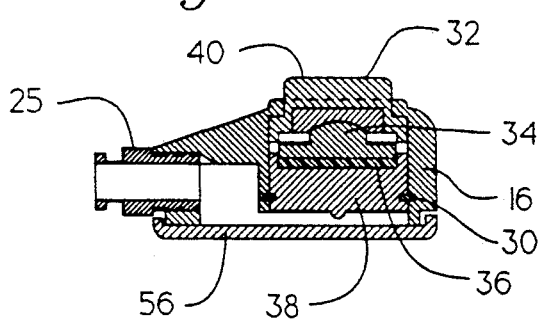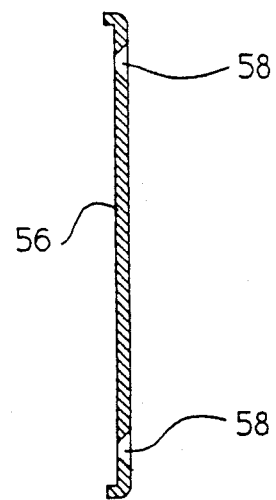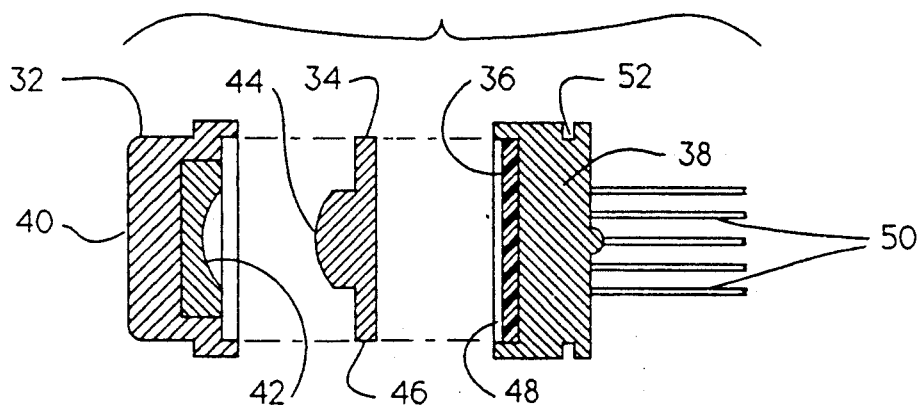

ISOMETRIC FORCE MEASURING DEVICE

BACKGROUND OF THE INVENTION

1. Field of the Invention

The present invention is directed generally to instruments for evaluating strength and, more specifically, to instruments for evaluating the strength of human fingers.

2. Description of the Background

Evaluation of the hands and the larger upper extremities, as currently performed in clinics and hospitals, consists of measurements of strength, range of motion, nerve sensation and graphic depiction of deformities of the hand, arm and shoulder. These measurements are required for pre-operative, post-operative, and periodic assessment of functional abnormality. To meet the requirements of most health and workman's compensation insurance, these measurements are standardized and reported in a consistent format throughout the United States. Evaluation techniques in other countries are quite similar, with expected changes in measurement units and reporting format.

The pinch meter is used to assess pinch strength. Pinch strength is important because it is one measure of the functionality of the fingers in conjunction with the opposed thumb. Because of its importance, three different measurements of pinch strength are usually taken: three point (thumb opposed by three fingers), four point (thumb opposed by four fingers), and key (thumb opposed laterally by all fingers as when holding a key). Pinch strength is measured in pounds or kilograms, and the typical range of value is from zero to thirty-five pounds.

Pinchmeters within the current state of the art are generally constructed of a metal beam having a "C" shaped cross-section. When a pinch force is applied to the top and bottom of the "C," the pinchmeter is deflected inward in proportion to the pinch strength applied. The deflection is measured by a dial indicator which is calibrated to read the pinch force exerted in either pounds or kilograms. The pinchmeter has an indicated surface for placing the thumb and fingers to obtain an accurate reading. Examples of this type pinch meter include the PC 5036M pinch gage manufactured by Therapeutic Equipment Corporation, 60 Page Road, Clifton, N.J. 07012, and the B&L Pinch Meter manufactured by North Coast Medical, Inc., 450 Salmar Avenue, Campbell, Calif. 95008. A variation of this type includes the PC 5030HPG hydraulic pinch gage manufactured under the Jamar ® name by the J.A. Preston Corporation, 60 Page Road, Clifton, N.J. 07012.

Another type of pinchmeter recently introduced is the electronic pinchmeter. It has the electronics and force sensing technology to produce a digital reading of the pinch force applied. This type of pinchmeter typically uses a strain gage to measure deflection and converts that reading into a voltage which can be read by other devices, such as computers. These pinchmeters are constructed out of molded plastic and metal, and contain a circuit board with the electronic components necessary for the computer interface. An example of this type of pinch meter includes the PC 5030 PA digital pinch gage manufactured under the Jamar ® name by the J.A. Preston Corporation.

Because of the importance of pinch strength to the functionality of the hand through the pinching movement of the fingers in relation to the thumb, and the importance of this measurement in evaluating impairment of the hand, it is imperative that measurement of pinch strength be accurate. Because the examiner can't determine whether a patient is or is not applying the maximum strength he is able to apply at the time of the examination, there is a need for a pinch meter with respect to which a patient is unable to accurately sense and then repeat application of a submaximal amount of pinch force. If a patient can accurately sense the measurement being taken, as by sensing the amount of movement of the component parts of the pinchmeter or by other sensory feedback, his ability to repeatedly apply a submaximal pinch force and to therefore "cheat" or "fake" the measurement is enhanced. There is also a need for a pinch meter that is shaped in a way that will allow the patient to easily place the fingers and thumb so as to accommodate all three of the primary pinch measurements and which will likewise avoid inaccuracies induced by minor misalignment of the thumb and fingers on the device itself.

SUMMARY OF THE PRESENT INVENTION

The present invention, in its broadest form, is directed to an isometric force-measuring device comprised of first and second opposed force-bearing surfaces. An incompressible, nonfluid, elastomeric material is positioned between the first and second surfaces. The material is capable of building up pressure to resist the force applied to the force-bearing surfaces. A pressure transducer is responsive to the pressure built up in the material for producing an output signal representative of the force.

According to one embodiment of the invention, the isometric force-measuring device may take the form of a pinch meter. In that embodiment, a push button, adapted for receiving a force from a user's thumb is provided. A base plate adapted for receiving a force from at least one of the users fingers is also provided. An incompressible, elastomeric material is positioned between the push button and the base plate for building up pressure in response to the application of force to the push button and the base plate. The pressure transducer is responsive to the pressure stored in the material for producing an output signal representative of the force.

The isometric force-measuring device of the present invention provides significant advantages over the prior art. By measuring force through the cooperation of an incompressible material and a pressure transducer, the user receives no feedback with respect to the movement or bending of internal components. That makes "cheating" or "faking" of the measurement very difficult. Additionally, the device is constructed such that the force applied by the user's thumb is transmitted to the incompressible material while undesirable torque is prevented from influencing the measurement. Finally, the size of the base plate facilitates taking all of the major pinch strength measurements. Those and other advantages and benefits of the present invention will become apparent from the Detailed Description of The Preferred Embodiment hereinbelow.

BRIEF DESCRIPTION OF THE DRAWINGS

For the present invention to be clearly understood and readily practiced, a preferred embodiment will now be described, by way of example only, with reference to the accompanying figures wherein:

FIG. 3 is a top view of the isometric force-measuring device illustrated in FIG. 1;

FIG. 4 is a view of the device illustrated in FIG. 3 taken along the lines IV—IV;

FIG. 5 is a cross-sectional view of the device illustrated in FIG. 3;

FIG. 6 is a cross-sectional view of the base plate of the device illustrated in FIG. 3;

FIG. 7 is an exploded cross-sectional view of certain components of the isometric force-measuring device of the present invention.

DETAILED DESCRIPTION OF THE PREFERRED EMBODIMENT

Figure 1:
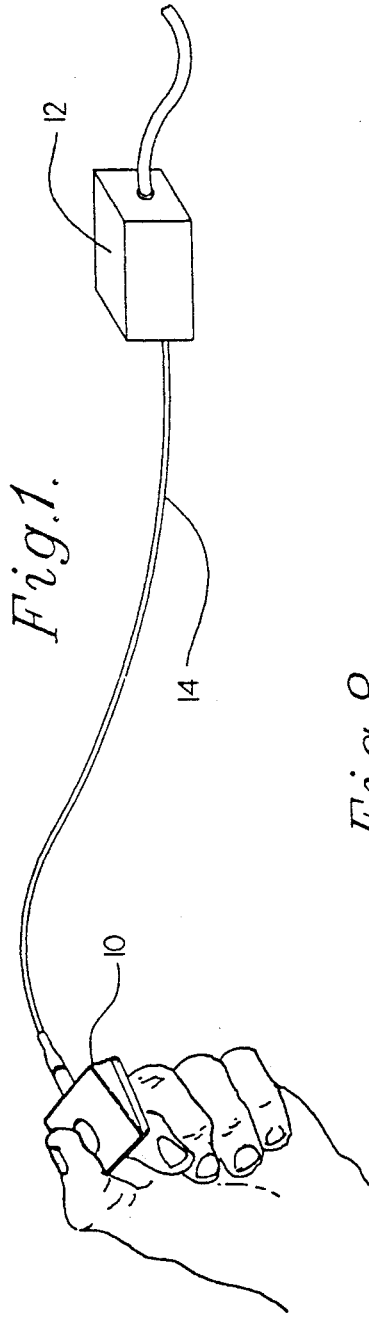
FIG. 1 is a perspective view of an isometric force-measuring device and power supply constructed according to the teachings of the present invention.

FIG. 1 is a prospective view of an isometric force-measuring device 10 and an interface/power supply 12 constructed according to the teachings of the present invention. The device 10 is connected to the interface/power supply 12 through a cable 14. As illustrated in FIG. 1, the device 10 is being used to perform a key measurement. However, the present invention is constructed to enable the performance of all the various common force measurements taken in conjunction with the thumb and fingers.

Figure 2:
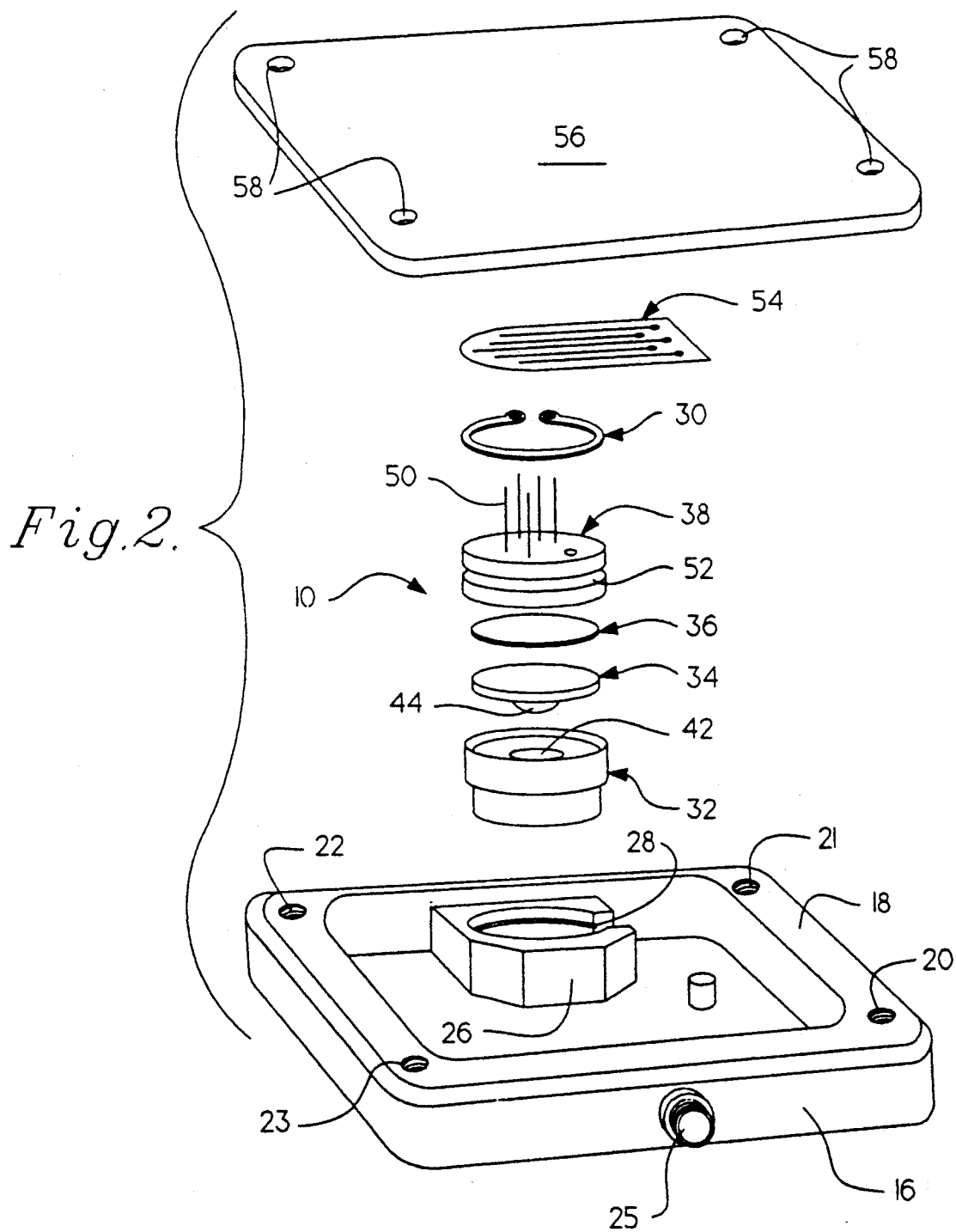
FIG. 2 is an exploded view of the isometric force-measuring device illustrated in FIG. 1.

FIG. 2 is an exploded view of an isometric force-measuring device 10 illustrated in FIG. 1. In FIG. 2, the device 10 is comprised of a main housing 16. The main housing 16 has an interior surface 18 carrying four threaded holes 20, 21, 22, and 23. The main housing 16 also has a port 25 which connects to the cable 14. The main housing 16 also has a push button support structure 26, which contains an indentation 28 for a snap ring 30. FIG. 3 is a top view of the isometric force-measuring device 10 looking down on the main housing 16.

The next group of components comprising the device 10 are the button assembly 32, thrust washer 34, a washer shaped component comprised of elastomeric material 36, and a pressure transducer 38. That group of components is illustrated in FIG. 7 as well as FIG. 2. The button assembly 32 is seen in FIG. 7 to have a first end 40 adapted for receiving force applied by a user's thumb. The opposite end of button assembly 32 has a concaved surface 42 formed therein which acts as a socket for a ball and socket type joint formed by the button assembly 32 and the thrust washer 34. The thrust washer 34 has a ball portion 44 molded therein which forms the ball portion of the ball and socket joint formed by the thrust washer 34 and button assembly 32. The ball portion 44 of the thrust washer 34 is supported by a circular base 46.

The sensor 38 is a commercially available sensor which may be, for example, a NOVA NPI-19A-172G. It is known that such sensors are received from the manufacturer with a circular depression 48 seen in FIG. 7. Within that circular depression the incompressible, elastomeric material 36 is molded. For example, the material may be a silicon RTV rubber which is molded in place. As can be seen from FIG. 7, the elastomeric material 36 does not completely fill the circular depression 48. That enables the base 46 of the thrust washer 34 to also be seated within circular depression 48 as seen in FIGS. 4 and 5. The sensor 38 has a number of electrical leads 50 extending therefrom as is known.

The sensor 38 has an indentation 52 formed therein. The snap ring 30 cooperates with both the indentation 52 of the sensor 38 and the indentation 28 of the push button support structure 26 to restrain the movement of the button assembly 32, thrust washer 34, and sensor 38 in one direction. Movement of the aforementioned components in the other direction is restrained by the configuration of the main housing 16 as seen in FIG. 4.

Completing the description of the device 10 illustrated in FIG. 2, a flexible PC board 54 is provided to connect the leads 50 of pressure sensor 38 to a rigid PC board 82, shown in FIG. 4. A base member 56, seen in cross section in FIG. 6, completes the assembly. The base member may, for example, be 2.5 inches long, 1.4 inches wide, and 0.063 inches thick. The base member 56 is attached to the main housing 16 through the cooperation of four screws (not shown) extending through openings 58 in the base member 56 and received by the threaded holes 20 through 23. Through that construction, the base member 56 can be quickly removed for servicing or replacement of parts.

The device 10 of the present invention uses a high durometer (65 Shore A) silicon rubber (elastomer) as a "fluid" for converting a force to a pressure which is subsequently measured by the pressure transducer 38. That novel use of a silicon rubber results in a design that requires no sealing to prevent fluid leakage and eliminates the required expensive close tolerances of mating parts for fluid retaining structures. The silicon rubber is a high viscosity (as compared to oil, water or gels) noncompressible "fluid" that can be sealed easily and cheaply at the time of assembly.

To prevent the high viscosity property of the silicon rubber from degrading the accuracy of the pressure transducer 38, the silicon rubber 36 should be molded directly into the pressure transducer 38 as previously stated. The thrust washer 34, which is pressed against the silicon rubber 36 upon depression of the button assembly 32, has a specially designed base surface 44 which prevents any flowing of the silicon rubber 36 which would cause further inaccuracy of the transducer. The thrust washer 34 and button assembly 32 provide a ball and socket joint to prevent any moments (torques) generated by the force applied to the button assembly 32 from being transmitted to the silicon rubber 36. Thus, the device 10 of the present invention uses a novel approach to force-measuring by: using an elastomeric material 36 instead of a hydraulic fluid, molding the material 36 directly into the sensor 38, using a specially designed thrust washer 34 which, together with the button assembly 32, acts as a piston, to increase the accuracy of the device 10 to less than 1% total error.

Figure 8:
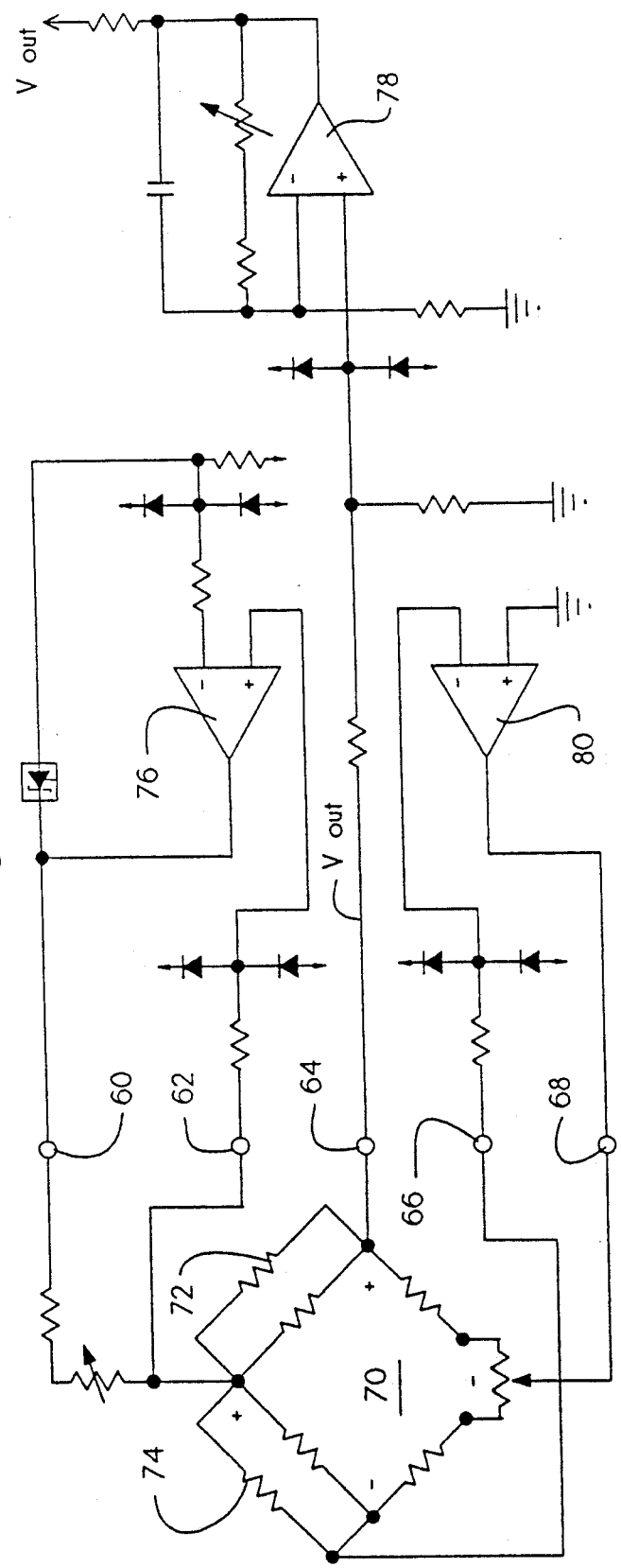
FIG. 8 is an electrical schematic of the isometric force-measuring device and power supply of the present invention.

FIG. 8 is an electrical schematic of the isometric force-measuring device 10 and interface/power supply 12 of the present invention. The cable 14 is seen as being a five conductor cable having conductors 60, 62, 64, 66, and 68. The circuitry contained within the device 10 is illustrated in the left portion of FIG. 8 and is comprised generally of the sensor 38, represented by the bridge 70, and two temperature compensation resistors 72 and 74. An operational amplifier 76, and its associated components, provides a constant adjustable current to the device 10 through the conductor 60. An operational amplifier 80 has an inverting input terminal connected to the conductor 66 and its non-inverting input terminal connected to conductor 68. The operational amplifier 80 provides a current sink to balance the bridge circuit.

An output signal $V_{out}$ of the device 10 is available on conductor 64 and is input to an operational amplifier 78 which determines the gain of the output signal. The output signal $V_{out}$ available at an output terminal of the operational amplifier 78 is an analog voltage representative of the pressure sensed by the transducer 38 and is therefore representative of the force applied to the device 10. That signal may be input to an analog-to-digital converter, a meter, a computer having an analog-to-digital converter card, or any similar device. Typically, the signal is input to some type of device which retains the highest force registered.

As is seen, the device 10 of the present invention provides an accurate measurement of the sensed force. The accuracy of that measurement is insured by the unique construction and interaction of the various components. In addition to the high accuracy, the novel use of the elastomeric material 36 in conjunction with the pressure transducer 38 makes it very difficult to "cheat" or "fake" readings because the user receives no tactile feedback from the device 10. The unique juxtapositioning of the push button assembly 32 and the base member 56, together with the sizing of the base member 56, allows for a wide range of force measurements.

While the present invention has been described in connection with an exemplary embodiment thereof, it will be understood that many modifications and variations will be readily apparent to those of ordinary skill in the art. This disclosure and the following claims are intended to cover all such modifications and variations.

What is claimed is:

1. A method for measuring an isometric force, said method comprising the steps of:

receiving a force from a user's thumb through a push button means;

receiving a force from at least one of a user's fingers through a plate means;

building up pressure in response to the application of force to said push button means and said plate means in an incompressible, elastomeric material positioned between said push button means and plate means without producing any tactile feedback to the user; and producing an output signal representative of said force through a pressure transducer means responsive to said pressure stored in said material.

* * * * *